US012285635B2

(12) United States Patent
Gaderlund et al.

(10) Patent No.: US 12,285,635 B2
(45) Date of Patent: *Apr. 29, 2025

(54) SINGLE-PASS IMAGING AND RADIATION TREATMENT DELIVERY VIA AN EXTENDED ROTATION GANTRY

(71) Applicant: Varian Medical Systems, Inc., Palo Alto, CA (US)

(72) Inventors: Blake Gaderlund, Mountain View, CA (US); Josh Star-Lack, Palo Alto, CA (US); John Van Heteren, Foster City, CA (US); Adam Wang, Menlo Park, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/111,560

(22) Filed: Feb. 18, 2023

(65) Prior Publication Data
US 2023/0201631 A1 Jun. 29, 2023

Related U.S. Application Data

(63) Continuation of application No. 17/200,888, filed on Mar. 14, 2021, now Pat. No. 11,583,704, which is a
(Continued)

(51) Int. Cl.
*A61N 5/10* (2006.01)
*A61B 6/00* (2024.01)
(Continued)

(52) U.S. Cl.
CPC ......... *A61N 5/1081* (2013.01); *A61N 5/1067* (2013.01); *A61B 6/032* (2013.01);
(Continued)

(58) Field of Classification Search
CPC .......... A61N 5/1081; A61N 2005/1054; A61N 2005/1061; A61N 5/1031; A61N 5/1038;
(Continued)

(56) References Cited

U.S. PATENT DOCUMENTS 4,063,097 A * 12/1977 Barrett ................. G06T 11/003
378/18
6,316,876 B1 11/2001 Tanabe
(Continued)

FOREIGN PATENT DOCUMENTS

| CN | 103517737 A | 1/2014 |
|----|-------------|--------|
| CN | 103889505 A | 6/2014 |
| CN | 105879245 A | 8/2016 |

OTHER PUBLICATIONS

International Search Report and Written Opinion of the International Searching Authority, International application No. PCT/US2019/043824, Oct. 15, 2019.
(Continued)

*Primary Examiner* — Chih-Cheng Kao
(74) *Attorney, Agent, or Firm* — SU IP CONSULTING

(57) ABSTRACT

An example method of radiation therapy in a radiation therapy system that includes a gantry with a treatment-delivering X-ray source and an imaging X-ray source mounted thereon is described. The method includes rotating the gantry in a first direction at a first rotational velocity about an open bore and concurrently rotating an annular support structure at a second rotational velocity about the open bore, wherein the second rotational velocity is less than the first rotational velocity. While continuing to rotate the gantry in the first direction about the open bore from a first position to a treatment position, the method also includes generating multiple images of a target volume disposed in the bore using the imaging X-ray source. Upon rotating the gantry to the treatment position, the method includes initi-
(Continued)

ating delivery of a treatment beam to the target volume with the treatment-delivering X-ray source.

20 Claims, 12 Drawing Sheets

Related U.S. Application Data continuation of application No. 16/180,021, filed on Nov. 5, 2018, now Pat. No. 10,960,232.

(60) Provisional application No. 62/711,483, filed on Jul. 28, 2018.

(51) Int. Cl.
   *A61B 6/03* (2006.01)
   *G06T 7/00* (2017.01)
   *G06T 11/00* (2006.01)

(52) U.S. Cl.
   CPC ............ *A61B 6/541* (2013.01); *A61N 5/1031* (2013.01); *A61N 5/1038* (2013.01); *A61N 5/1039* (2013.01); *A61N 5/1049* (2013.01); *A61N 2005/1054* (2013.01); *A61N 2005/1061* (2013.01); *A61N 5/107* (2013.01); *A61N 5/1071* (2013.01); *G06T 7/0012* (2013.01); *G06T 11/008* (2013.01); *G06T 2207/10081* (2013.01); *G06T 2207/20081* (2013.01)

(58) Field of Classification Search
   CPC .. A61N 5/1039; A61N 5/1049; A61N 5/1067; A61N 5/107; A61N 5/1071
   See application file for complete search history.

(56) References Cited

U.S. PATENT DOCUMENTS

| | | | |
|---|---|---|---|
| 10,960,232 B2 * | 3/2021 | Gaderlund | A61N 5/1067 |
| 11,583,704 B2 * | 2/2023 | Gaderlund | A61N 5/1081 |
| 2005/0201509 A1 | 9/2005 | Mostafavi et al. | |
| 2010/0183118 A1 | 7/2010 | Star-Lack et al. | |
| 2011/0085640 A1 | 4/2011 | Fadler | |
| 2011/0210261 A1 | 9/2011 | Maurer, Jr. | |
| 2013/0158382 A1 | 6/2013 | Chao | |
| 2016/0193482 A1 | 7/2016 | Fahrig et al. | |
| 2018/0056090 A1 * | 3/2018 | Jordan | A61N 5/1039 |
| 2020/0030636 A1 | 1/2020 | Gaderlund et al. | |
| 2020/0227184 A1 | 7/2020 | Purwar et al. | |

OTHER PUBLICATIONS

Holger R. Roth et al., "DeepOrgan: Multi-Level Deep Convolutional Networks for Automated Pancreas Segmentation", MICCAI 2015, Part I, 2015, pp. 556-564, Springer International Publishing Switzerland.

Özgün Cicek et al., "3D U-Net: Learning Dense Volumetric Segmentation from Sparse Annotation", MICCAI 2016, Jun. 21, 2016.

Jelmer M. Wolterink et al., "Deep MR to CT Synthesis using Unpaired Data", MICCAI 2017 Workshop on Simulation and Synthesis in Medical Imaging, Aug. 3, 2017.

Sara Sabour et al., "Dynamic Routing Between Capsules", 31st Conference on Neural Information Processing Systems (NIPS 2017), 2017.

Snehashis Roy et al., "Synthesizing CT from Ultrashort Echo-Time MR Images via Convolutional Neural Networks", International Workshop on Simulation and Synthesis in Medical Imaging (SASHIMI 2017), Jul. 27, 2018.

Fausto Milletari et al., "V-Net: Fully Convolutional Neural Networks for Volumetric Medical Image Segmentation", Jun. 15, 2016.

Can Zhao et al., "A Supervoxel Based Random Forest Synthesis Framework for Bidirectional MR/CT Synthesis", Simul Synth Med Imaging, Sep. 2017.

Jeffrey Neilson et al., "Design of RF Feed System and Cavities for Standing-wave Accelerator Structure", Nuclear Instruments and Methods in Physics Research A 657, 2011, pp. 52-54.

H Wang et al., "SU-F-J-109: Generate Synthetic CT From Cone Beam CT for CBCT-Based Dose Calculation", The International Journal of Medical Physics Research and Practice, Jun. 7, 2016, vol. 43, Issue 6.

Mattias P. Heinrich et al., "BRIEFnet: Deep Pancreas Segmentation Using Binary Sparse Convolutions", MICCAI 2017 Conference paper, Sep. 4, 2017, pp. 329-337.

Guang-Hong Chen et al., "Prior image constrained compressed sensing (PICCS): A method to accurately reconstruct dynamic CT images from highly undersampled projection data sets", Medical Physics, Feb. 2008, pp. 660-663, vol. 35, Issue 2.

* cited by examiner

SINGLE-PASS IMAGING AND RADIATION TREATMENT DELIVERY VIA AN EXTENDED ROTATION GANTRY

CROSS-REFERENCE TO RELATED APPLICATIONS

The present application is a continuation under 35 U.S.C. § 120 of U.S. patent application Ser. No. 17/200,888, filed Mar. 14, 2021, which is a continuation under 35 U.S.C. § 120 of U.S. patent application Ser. No. 16/180,021, filed Nov. 5, 2018, now U.S. Pat. No. 10,960,232, which claims the benefit of U.S. Provisional Application No. 62/711,483, filed Jul. 28, 2018. The aforementioned U.S. patent applications and U.S. Provisional Application, including any appendices or attachments thereof, are hereby incorporated by reference in their entirety.

BACKGROUND

Unless otherwise indicated herein, the approaches described in this section are not prior art to the claims in this application and are not admitted to be prior art by inclusion in this section.

Radiation therapy is a localized treatment for a specific target tissue, such as a cancerous tumor. Ideally, radiation therapy is performed on a planning target volume that spares the surrounding normal tissue from receiving doses above specified tolerances, thereby minimizing risk of damage to healthy tissue. Prior to the delivery of radiation therapy, an imaging system is typically employed to provide a three dimensional image of the target tissue and surrounding area. From such imaging, the size and mass of the target tissue can be estimated and an appropriate treatment plan generated and target volume determined.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues while radiation treatment is delivered to the planning target volume. IGRT incorporates imaging coordinates from the treatment plan to ensure the patient is properly aligned for treatment in the radiation therapy device.

SUMMARY

In accordance with at least some embodiments of the present disclosure, a radiation therapy system is configured to deliver radiation treatment over a 360-degree arc and to perform a prepended imaging process, in a single pass, via an extended rotation gantry. That is, while rotating the gantry in one direction about a bore of the radiation system, the radiation system generates multiple images of a target volume disposed in the bore using an imaging X-ray source mounted on the gantry. Then while continuing to rotate the gantry in the same direction, the radiation system delivers a treatment beam to the target volume using a treatment-delivering X-ray source mounted on the gantry, where the treatment beam is delivered from some or all of a 360-degree arc about the bore. Thus, the prepended imaging process and the delivery of radiation are performed in a single-pass of the gantry about a target volume, eliminating the need for a return stroke of the gantry for completion.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
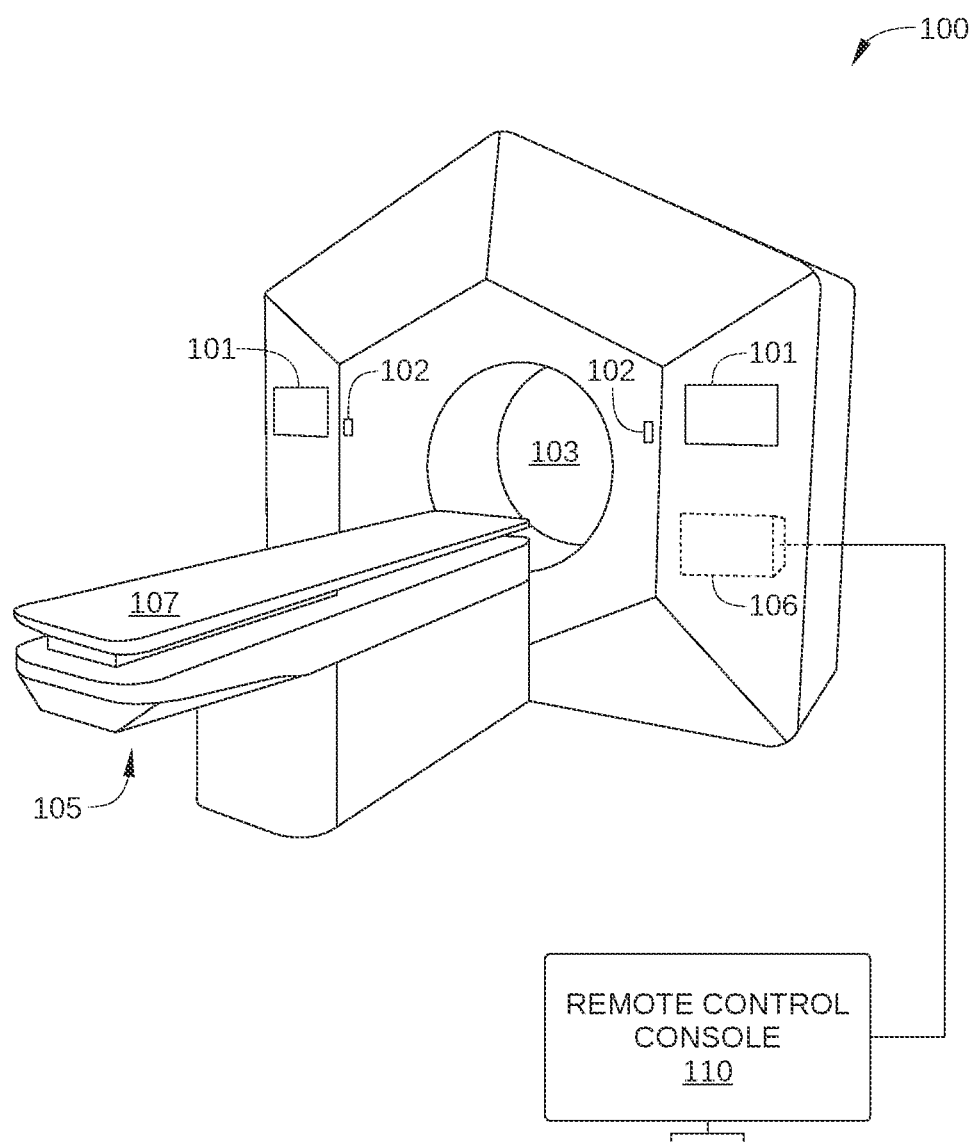
FIG. 1 is a perspective view of a radiation therapy system, according to one or more embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

In many radiation therapy systems, a volumetric arc therapy (VMAT) treatment is performed by rotating a treatment-delivering X-ray source through a 360-degree arc, so that a treatment beam can be delivered in the plane of the X-ray source rotation from any angle. Consequently, for such radiation systems, the gantry on which X-ray sources are mounted is typically designed for a 360-degree rotation about the bore of the system. Gantry rotation of greater than about 360 degrees is generally limited, due to interference of the liquid cooling hoses and bulky power cables coupled to the rotating gantry. As a result, any radiation treatment that requires greater rotation of the gantry about the bore of the system than a single 360-degree arc can be more time consuming, and therefore much more difficult to complete during a single breath-hold. This is because completion of a such a radiation treatment on a conventional system necessarily involves rotating the gantry through an arc to perform a first portion of the radiation treatment, stopping the rotation of the gantry, performing a return stroke by rotating the gantry back to an appropriate starting location, then completing the radiation treatment by rotating the gantry to perform a final portion of the radiation treatment.

In image guided radiation therapy (IGRT), two- and/or three-dimensional imaging is employed during a course of radiation treatment to improve the accuracy of the radiation field placement, and to reduce the exposure of healthy tissue during the radiation treatment. For example, a planned radiation treatment can be adapted based on detected intra-fraction motion and patient misalignment that may occur during the course of radiation treatment. Ideally, X-ray images of the treated area are acquired immediately prior to delivery of a treatment beam and during the same breath-hold that the treatment beam is delivered, to minimize intra-fraction motion of the treated area. For example, a cone beam computed tomography (CBCT) imaging process may be performed to generate the X-ray images of the treated area. However, CBCT and other prepended imaging procedures typically require rotation of the gantry through an arc of 90 degrees (given multiple X-ray imagers) to 180 degrees (given a single X-ray imager). Further, the delivery of the treatment beam generally requires an additional 360 degrees of gantry rotation. As a result, a gantry rotation of much more than 360 degrees is necessary to acquire X-ray images immediately prior to delivery of the treatment beam and during the same breath-hold. As set forth above, in conventional radiation systems, interference of the liquid cooling hoses and power cables coupled to the gantry typically occurs for gantry rotations of more than 360 degrees, thereby preventing conventional systems from performing such procedures in a single pass or stroke of the gantry.

In light of the above, there is a need in the art for improved systems and techniques for acquiring X-ray images and delivering of a treatment beam during a single patient breath-hold. According to embodiments of the present disclosure, a radiation therapy system is configured to deliver radiation treatment throughout a 360-degree arc and to perform a prepended imaging process, in a single pass, via an extended rotation gantry. One such embodiment is illustrated if FIG. 1.

FIG. 1 is a perspective view of a radiation therapy system 100, according to one or more embodiments of the present disclosure. Radiation therapy (RT) system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, a kilovolt (kV) X-ray source, an X-ray imager, and, in some embodiments, an MV electronic portal imaging device (EPID) (not shown for clarity).

Generally, RT system 100 is capable of Megavolt (MV) and kilovolt (kV) imaging techniques, to enable the treatment planner and physician to make clinical decisions that are most appropriate for the patient based on the anatomy of the patient. In some situations, a treatment plan can include kV imaging for improved visualization of soft tissue. For example, in some embodiments, RT system 100 is configured with cone beam computed tomography (CBCT) capability for visualization of soft tissue via kV images.

RT system 100 includes one or more touchscreens 101, couch motion controls 102, an open bore 103, a base positioning assembly 105, a couch 107 disposed on base positioning assembly 105, and an image acquisition and treatment control computer 106, all of which are disposed within a treatment room. Alternatively, in some embodiments, image acquisition and treatment control computer 106 is located outside the treatment room, such as a control room adjacent to the treatment room. RT system 100 further includes a remote control console 110, which is disposed outside the treatment room and enables treatment delivery and patient monitoring from a remote location. In some embodiments, RT system 100 further includes one or more cameras (not shown) in the treatment room for patient monitoring.

Base positioning assembly 105 is configured to precisely position couch 107 with respect to bore 103. Motion controls 102 include input devices, such as buttons and/or switches, that enable a user to operate base positioning assembly 105 to automatically and precisely position couch 107 to a predetermined location with respect to bore 103. Motion controls 102 may also enable a user to manually position couch 107 to a specific location. Generally, base positioning assembly 105 is configured to position a patient on couch 107 so that a target region of the patient is at or near an isocenter about which the LINAC, EPID, kV X-ray source, and X-ray imager are rotated during RT treatment. Used in conjunction with anatomical imaging of the patient on the day of treatment, base positioning assembly 105 can adapt a treatment plan to minimize delivered dose error due to inter-fraction motion, which includes the observable changes in patient anatomy that can occur between daily patient scans. However, intra-fraction motion, which can significantly impact the outcomes of radiation treatment, can be more challenging to account for, and can result in under-dosing of the target and/or over-dosing of organs at risk. Intra-fraction motion includes anatomical variation due to periodic motion, such as respiratory or cardiac rhythm, or episodic motion (peristalsis, muscle relaxation, cough, involuntary movement, and the like), and can only be partially managed in conventional radiation therapy systems. For example, passive immobilization techniques can be employed, such as vac-lock bags, cradles, arm positioning handles, abdominal compression bars, etc., but these approaches have limited effectiveness. According to embodiments of the present disclosure, active motion tracking of and compensation for intra-fraction motion is facilitated by performing radiation treatment and prepended image acquisition during a single breath-hold in a single pass of an extended rotation gantry. One such embodiment is described below in conjunction with FIGS. 2A, 2B, 3, 4, 5, 6, and 7.

Figure 2A:
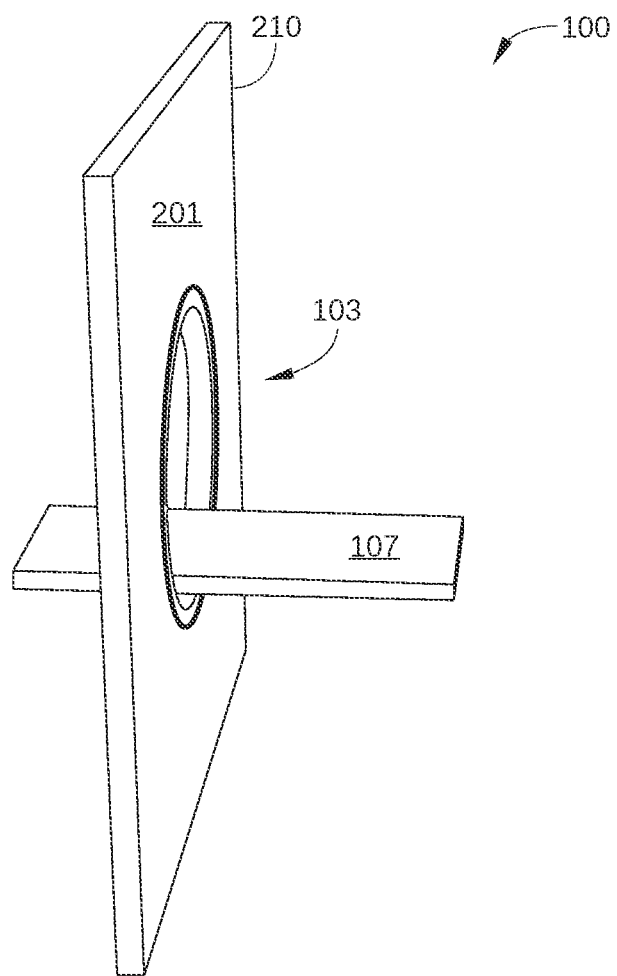
FIGS. 2A and 2B are schematic perspective views of the radiation therapy system of FIG. 1, according to various embodiments of the present disclosure.
Figure 2B:
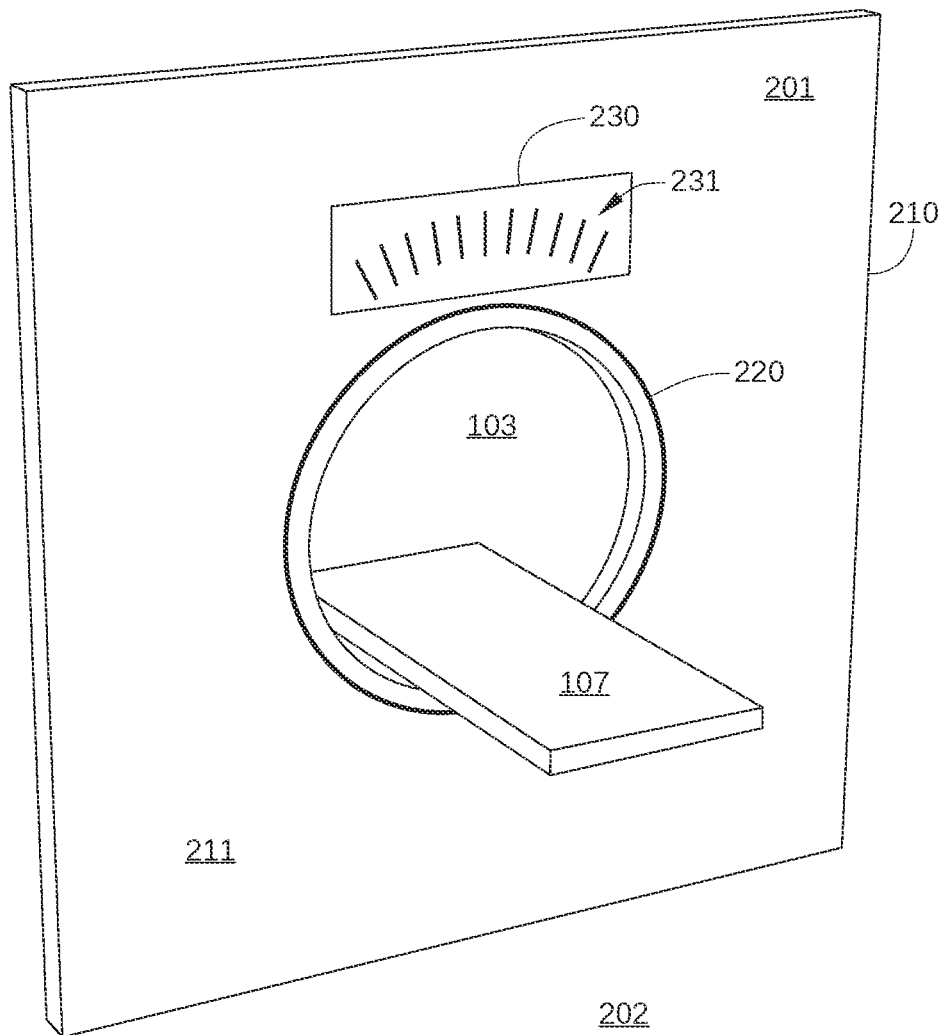

FIGS. 2A and 2B are schematic perspective views of RT system 100, according to various embodiments of the present disclosure. Various elements of RT system 100 are not shown in FIGS. 2A and 2B for clarity, including a rotatable gantry, system covers, cooling systems, and the like. As shown, RT system 100 includes a drive stand 210, a gantry bearing 220 disposed on a surface 201 of drive stand 210 and positioned around bore 103, and a force coil array 230 disposed on surface 211. Drive stand 210 is a fixed support structure for components of RT system 100, including a gantry, cooling systems of RT system 100, display screens, control electronics, and the like. Drive stand 210 rests on and/or is fixed to a support surface 202 that is external to RT system 100, such as a floor of an RT treatment facility. Gantry bearing 220 rotatably supports the gantry of RT system 100, and force coil array 230 includes a plurality of forcing coils 231 that cause the gantry to rotate. In some embodiments, forcing coils 231 are controlled by image acquisition and treatment control computer 106 in FIG. 1 to cause rotation of the gantry. Specifically, forcing coils 231, when properly energized, exert pushing or pulling forces on magnets coupled to the gantry.

Figure 3:
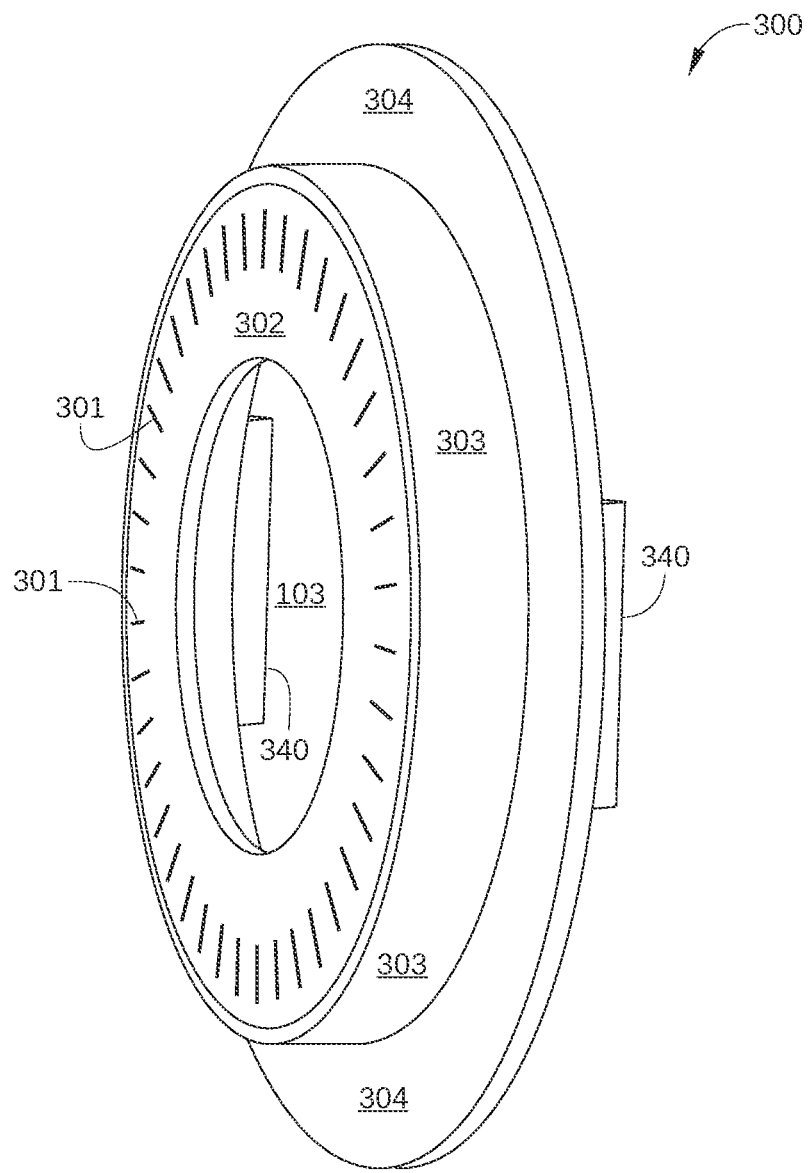
FIG. 3 is a schematic perspective view of a gantry of the radiation therapy system of FIG. 1, according to various embodiments of the present disclosure.

FIG. 3 is a schematic perspective view of a gantry 300 of RT system 100, according to various embodiments of the present disclosure. Gantry 300 is a rotatable support structure on which components 340 are mounted. Components 340 include systems and devices of RT system 100 that are rotated about bore 103 during RT treatment. Components 340 include heat-generating systems and/or electrically powered systems, such as a LINAC, EPID, kV X-ray source, and/or X-ray imager. Gantry 300 includes a plurality of magnets 301, such as permanent magnets, affixed to a surface 302 that faces surface 201 of drive stand 210 (shown in FIG. 2B). Magnets 301 interact with forcing coils 231 of force coil array 230 (shown in FIG. 2B) to cause rotation of gantry 300. In some embodiments, gantry 300 further includes a conduit management surface 303 on which one or more flexible utility conduits (not shown) are collected or retrieved from as gantry 300 rotates from one rotational position to another rotational position. In some embodiments, gantry 300 further includes a gantry flange 304 that prevents flexible utility conduits collected on conduit management surface 303 from being displaced off of conduit management surface 303 during rotation of gantry 300. Such flexible utility conduits, and the interactions thereof with conduit management surface 303, are described below in conjunction with FIGS. 4, 5, 6A, 6B, and 6C.

Figure 4:
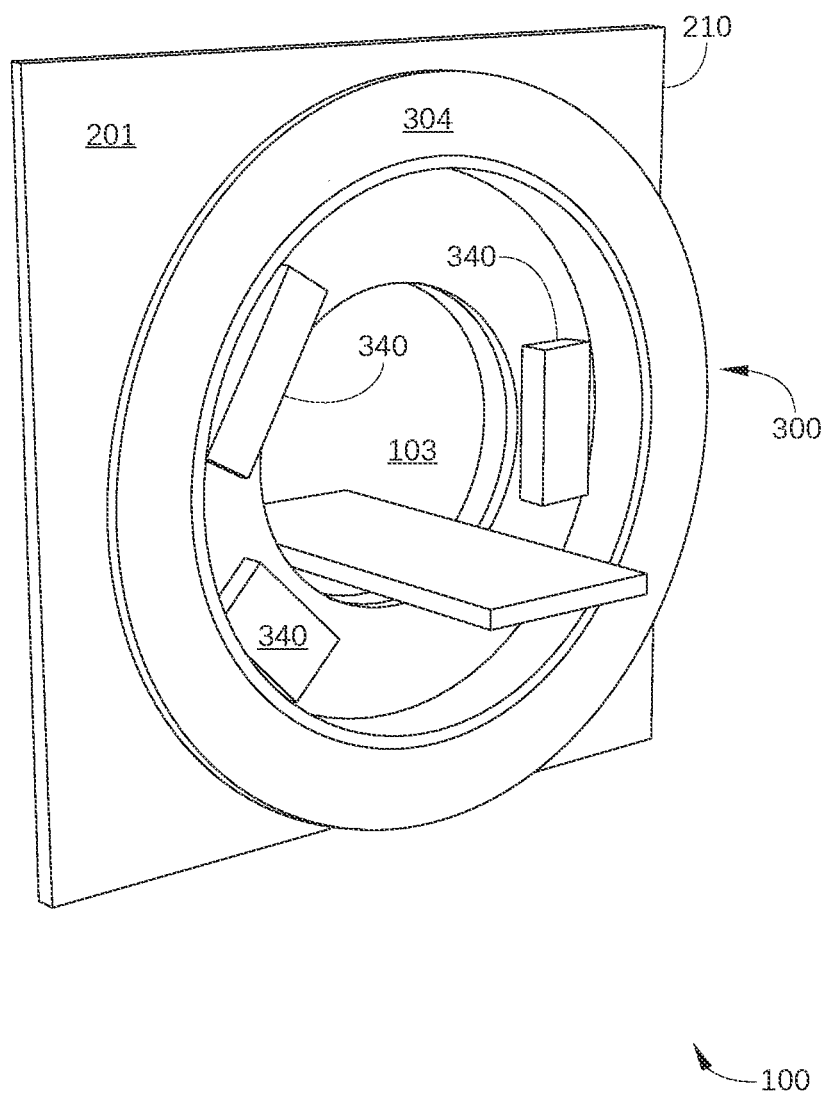
FIG. 4 is a schematic perspective view of a gantry mounted on a surface of a drive stand, according to various embodiments of the present disclosure.

FIG. 4 is a schematic perspective view of gantry 300 mounted on surface 201 of drive stand 210, according to various embodiments of the present disclosure. Force coil array 230 (see FIG. 2B) and conduit management surface 303 (see FIG. 3) are obscured in FIG. 4 by gantry flange 304. According to embodiments of the present disclosure, gantry 300 is configured to rotate continuously in a single direction through an arc that is significantly greater than 360 degrees, for example 480 degrees, 540 degrees, or the like. Thus, gantry 300 enables acquiring X-ray images and delivery of a treatment beam during a single pass (or stroke) of gantry 300. As a result, completing acquisition of X-ray images and the subsequent delivery of a treatment beam during a single patient breath-hold is greatly facilitated.

Figure 5:
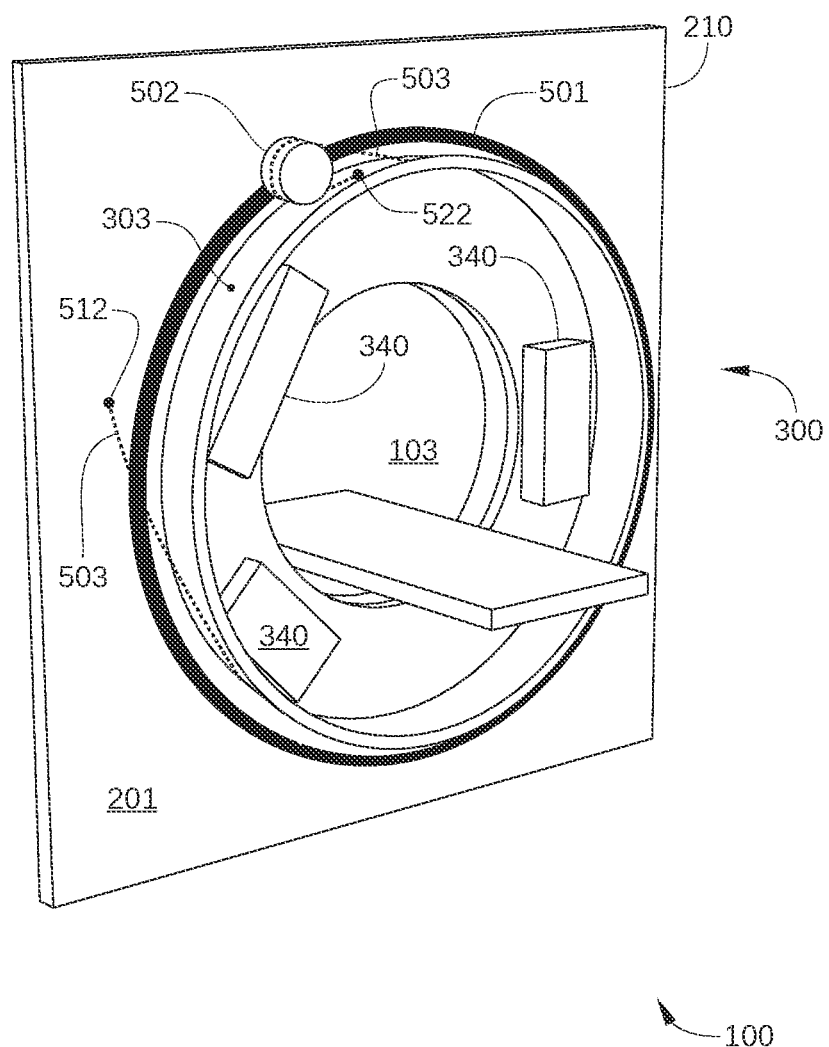
FIG. 5 is another schematic perspective view of a gantry mounted on a surface of a drive stand, according to various embodiments of the present disclosure.

FIG. 5 is another schematic perspective view of gantry 300 mounted on surface 201 of drive stand 210, according to various embodiments of the present disclosure. In FIG. 5, gantry flange 304 is not shown, so that conduit management surface 303 and an annular support structure 501 (solid) are visible. A guide wheel 502 is mounted on annular support structure 501, and a flexible utility conduit 503 is coupled to guide wheel 502 and is also visible.

Like gantry 300, annular support structure 501 is rotatably coupled to drive stand 210, and is configured to rotate about bore 103 of RT system 100 during radiation treatment. More specifically, annular support structure 501 is configured to rotate in the same direction that gantry 300 rotates about bore 301, but at half the rotational velocity. For example, when gantry 300 rotates clockwise about bore 301 at 4 RPM, annular support structure 501 is configured to rotate clockwise (or counterclockwise) about bore 301 at 2 at RPM. Similarly, when gantry 300 rotates counterclockwise about bore 301 at a certain rotational velocity, annular support structure 501 is configured to rotate counterclockwise about bore 301 at one half that rotational velocity. Furthermore, annular support structure 501 is configured to support and rotationally displace guide wheel 502. That is, as annular support structure 501 rotates about bore 103, guide wheel 502 is displace rotationally about bore 103.

Guide wheel 502 is a rotatable conduit management cylinder that is rotatably coupled to annular support structure 501. Guide wheel 502 is configured to guide flexible utility conduit 503 (dashed line) from a fixed connection point on drive stand 210 to a fixed connection point on gantry 300. More specifically, flexible utility conduit 503 is routed from the fixed connection point on drive stand 210, around guide wheel 502 for one-half turn, along conduit management surface 303 of gantry 300, to the fixed connection point on gantry 300.

Flexible utility conduit 503 includes one or more hoses for cooling liquid and/or power cables (radio frequency, alternating current, direct current, and the like). Flexible utility conduit 503 can be a single hose or power cable, or a bundle of multiple hoses and/or power cables. Thus, flexible utility conduit 503 routes one or more utilities from drive stand 210 to gantry 300. One end of flexible utility conduit 503 is coupled to a connector 512 mounted on drive stand 210, which remains motionless during operation of RT system 100. In addition, an opposite end of flexible utility conduit 503 is coupled to a connector 522 mounted on gantry 300, which does not remain motionless during operation of RT system 100. Instead, connector 522 is rotationally displaced about bore 103 as gantry 300 rotates about bore 103. As is evident from FIG. 5, if flexible utility conduit 503 were routed directly to connector 522 from connector 512, instead of being routed around guide wheel 502, rotation of gantry 300 of greater than about 360 degrees is likely to cause fouling of flexible utility conduit 503 and/or interference with rotation of gantry 300. However, according to embodiments of the present disclosure, flexible utility conduit 503 is routed to connector 522 from connector 512 via guide wheel 502, which rotationally translates about bore 103 when gantry 300 rotates about bore 103. As a result, gantry 300 can rotate continuously in a single direction through an arc that is significantly greater than 360 degrees, for example 480 degrees or 540 degrees, without interference from flexible utility conduit 503. One such embodiment is illustrated in FIGS. 6A, 6B, and 6C.

Figure 6A:
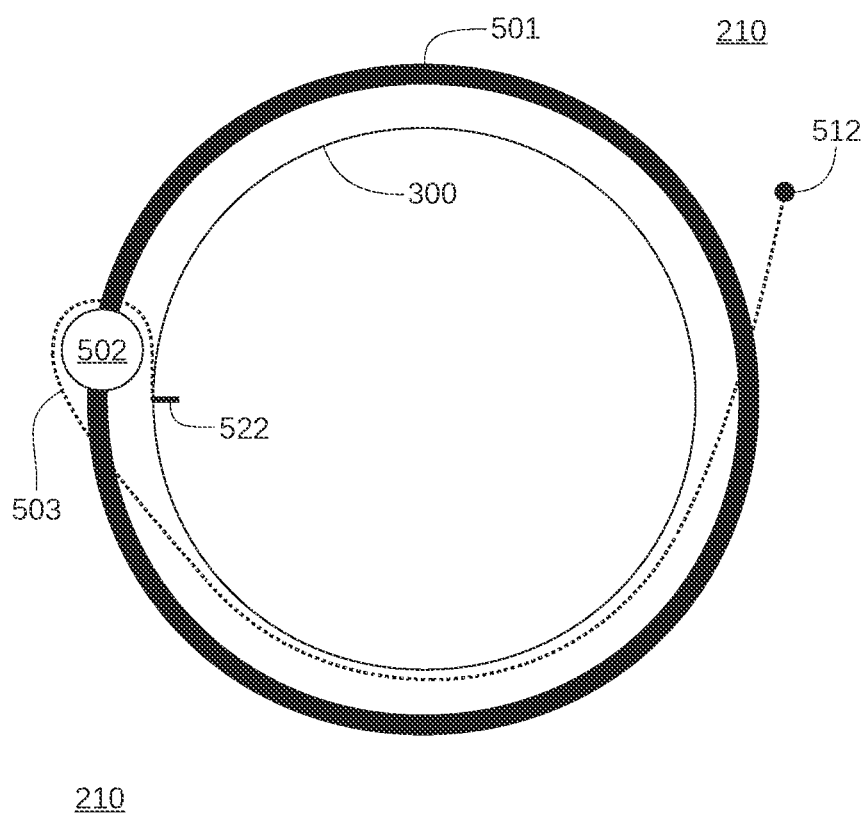
FIG. 6A schematically illustrates the routing of a flexible utility conduit when a gantry is disposed at one extent of the possible rotation of the gantry, according to an embodiment of the present disclosure.

FIG. 6A schematically illustrates the routing of flexible utility conduit 503 when gantry 300 is radially oriented at one extent of the possible rotation of gantry 300, according to an embodiment of the present disclosure. In FIG. 6A, gantry 300 is rotated to the limit of clockwise rotation for gantry 300 and annular support structure 501 is at the limit of clockwise rotation for annular support structure 501. As a result, annular support structure 501 (solid) is oriented so that guide wheel 502 (which is mounted on annular support structure 501) is disposed radially proximate connector 522 (which is mounted on gantry 300). Flexible utility conduit 503 is routed for approximately one-half turn around guide wheel 502. In the embodiment illustrated in FIG. 6A, connector 512, which is mounted on drive stand 210, is radially displaced (counterclockwise) from guide wheel 502 by approximately 225 degrees when gantry 300 is at the maximum extent of clockwise rotation shown in FIG. 6A. In other embodiments, connector 512 can be mounted on drive stand 210 at a location that is radially displaced from guide wheel 502 by as much as about 350 degrees.

Figure 6B:
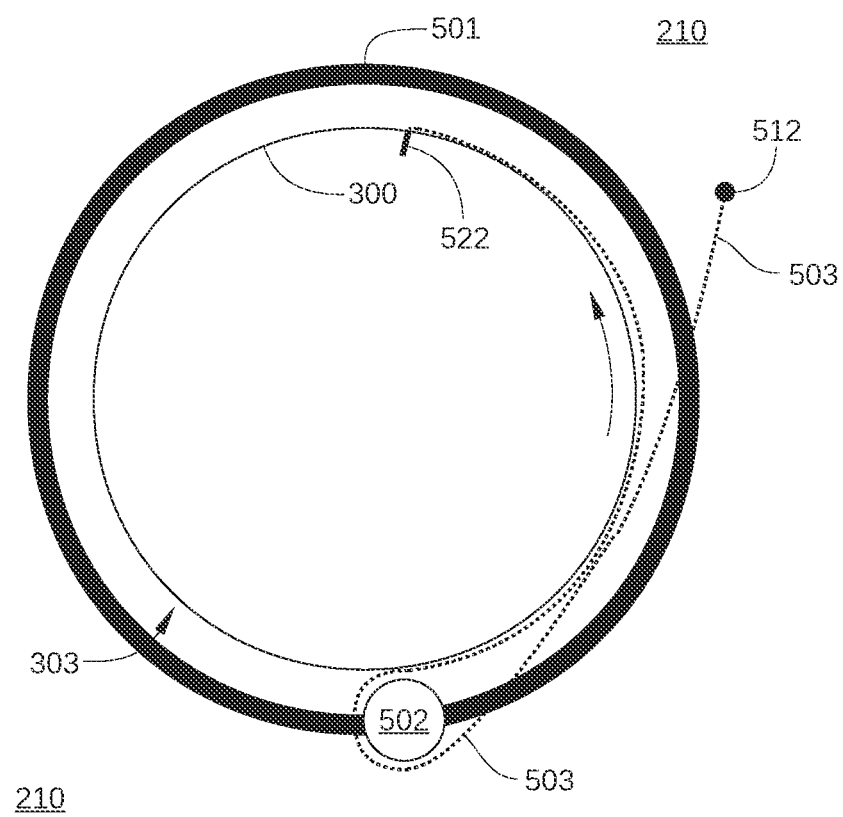
FIG. 6B schematically illustrates the routing of a flexible utility conduit when a gantry is disposed between the limit of clockwise rotation of the gantry and the limit of counterclockwise rotation of the gantry, according to an embodiment of the present disclosure.

FIG. 6B schematically illustrates the routing of flexible utility conduit 503 when gantry 300 is disposed between the limit of clockwise rotation of gantry 300 and the limit of counterclockwise rotation of gantry 300, according to an embodiment of the present disclosure. In FIG. 6B, gantry 300 has rotated counterclockwise 270 degrees from the position shown in FIG. 6A. As a result, annular support structure 501, which is configured to rotate in the same direction as gantry 300 but at half the rotational velocity, is oriented so that guide wheel 502 is radially disposed at about halfway between the current radial location of connector 522 if FIG. 6B and the original radial location of connector 522, shown in FIG. 6A.

Figure 6C:
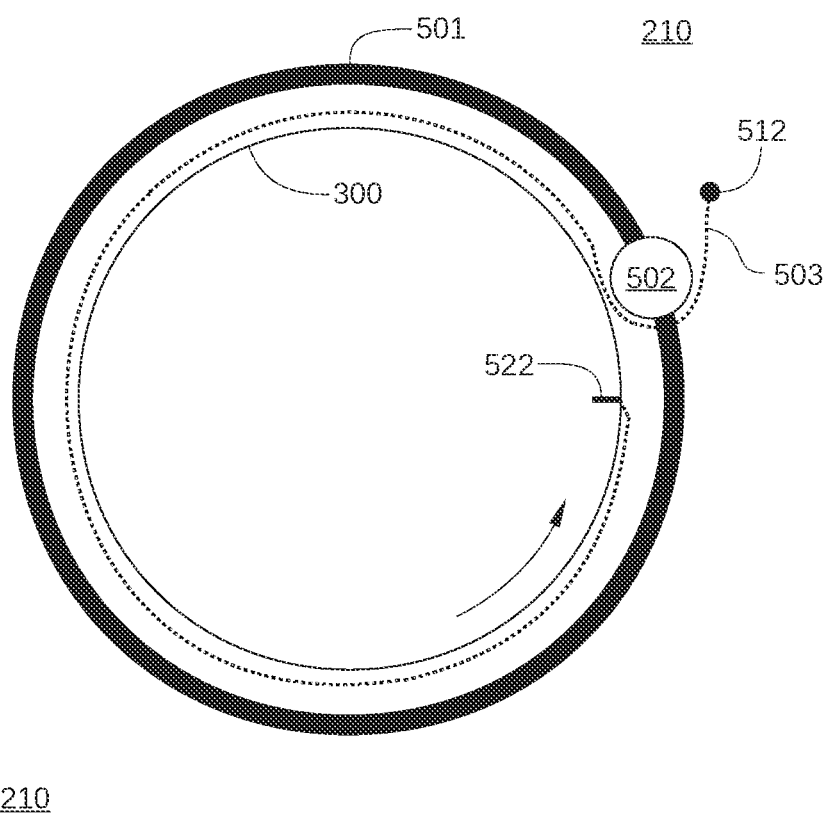
FIG. 6C schematically illustrates the routing of a flexible utility conduit when a gantry is disposed at the limit of counterclockwise rotation of the gantry, according to an embodiment of the present disclosure.

FIG. 6C schematically illustrates the routing of flexible utility conduit 503 when gantry 300 is disposed at the limit of counterclockwise rotation of gantry 300, according to an embodiment of the present disclosure. In FIG. 6C, gantry 300 has rotated counterclockwise an additional 270 degrees from the position shown in FIG. 6B, and is at the limit of counterclockwise rotation for gantry 300. Annular support structure 501 rotated counterclockwise an additional 135 degrees, and is at the limit of counterclockwise rotation for annular support structure 501. As a result, annular support structure 501 is oriented so that guide wheel 502 (which is mounted on annular support structure 501) is disposed radially proximate connector 512 (which is mounted on drive stand 210).

As illustrated in FIGS. 6A, 6B, and 6C, flexible utility conduit 503 is routed for a half-turn around guide wheel 502, and guide wheel 502 is rotationally displaced in the same direct that gantry 300 is displaced. Consequently, when gantry 300 rotates during operation, a "wind-up" action is effectuated with respect to flexible utility conduit 503. That is, when gantry 300 is rotated to cause connector 522 to move toward connector 512, slack in flexible utility conduit 503 that would normally be generated is instead drawn across conduit management surface 303. As a result, gantry 300 can rotate in a single direction through an arc greater than 360 and up to approximately 700 degrees without the risk of slack loops of flexible utility conduit 503 catching on portions of gantry 300 or drive stand 210, or otherwise interfering with motion of gantry 300.

In the embodiment illustrated in FIGS. 6A, 6B, and 6C, a single guide wheel 502 is coupled to annular support structure 501, and a single flexible utility conduit 503 is guided from a fixed connection point on drive stand 210 to a fixed connection point on gantry 300 via guide wheel 502. In other embodiments, multiple flexible utility conduits are each guided from a respective fixed connection point on drive stand 210 to a respective fixed connection point on gantry 300 via a respective guide wheel. Thus, in such embodiments, multiple guide wheels are rotatably mounted on annular support structure 501.

In some instances, different portions of flexible utility conduit 503 can come in contact with each other during rotation of gantry 300. One such instance in depicted in FIG. 6B, in which a portion of flexible utility conduit 503 leading from connector 512 contacts a portion of flexible utility conduit 503 disposed on conduit management surface 303 of gantry 300. These contacting portions of flexible utility conduit 503 are moving relative to each other, since conduit management surface 303 is rotating past the portion of flexible utility conduit 503 leading from connector 512. Thus, surfaces of flexible utility conduit 503 can undergo additional wear during use. According to some embodiments of the present disclosure, RT system 100 includes one or more cable separators to prevent such wear. One such embodiment is illustrated in FIG. 7 and another is illustrated in FIG. 8.

Figure 7:
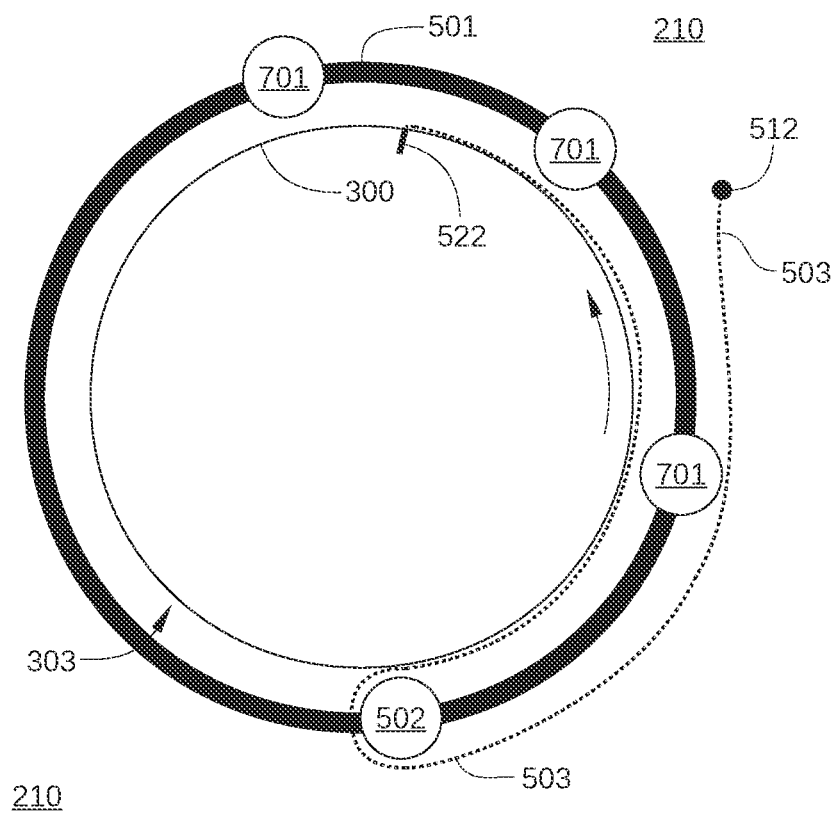
FIG. 7 schematically illustrates the routing of a flexible utility conduit proximate a gantry, according to an embodiment of the present disclosure.

FIG. 7 schematically illustrates the routing of flexible utility conduit 503 proximate gantry 300, according to an embodiment of the present disclosure. In the embodiment illustrated in FIG. 7, RT 100 includes one or more separating wheels 701, which are rotatably coupled to annular support structure 501 as shown. Thus, separating wheels 701 are positioned between a portion of flexible utility conduit 503 that is disposed against conduit management surface 303 and a portion of flexible utility conduit 503 that leads from guide wheel 502 to connector 512. As a result, flexible utility conduit 503 undergoes less wear during rotation of gantry 300.

Figure 8:
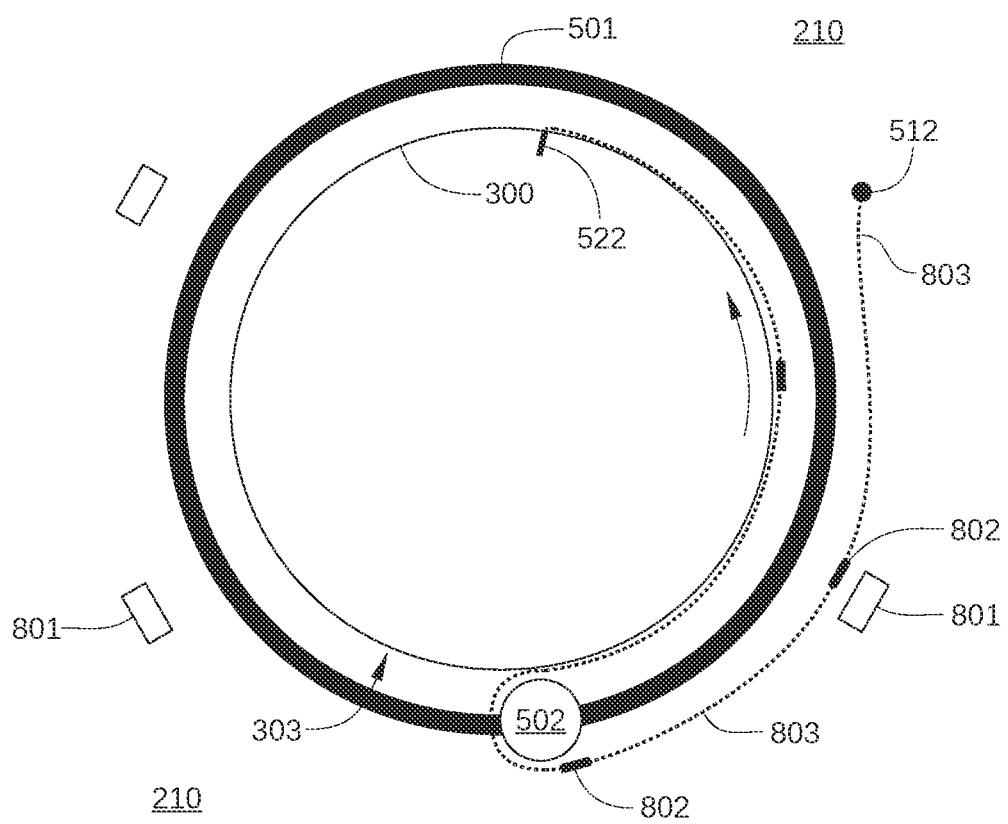
FIG. 8 schematically illustrates the routing of a flexible utility conduit proximate a gantry, according to another embodiment of the present disclosure.

FIG. 8 schematically illustrates the routing of flexible utility conduit 503 proximate gantry 300, according to another embodiment of the present disclosure. In the embodiment illustrated in FIG. 8, RT 100 includes one or more electromagnets 801, which are fixed to a static (non-rotating) surface of drive stand 210. In addition, a flexible utility conduit 803 is configured with one or more ferromagnetic plates 802. As shown, ferromagnetic plates 802 are coupled to an outer surface 804 of flexible utility conduit 803. In some embodiments, flexible utility conduit 803 is configured with a rectangular cross-section, which facilitates the coupling of ferromagnetic plates 802 to outer surface 804. In such embodiments, a computing device, such as image acquisition and treatment control computer 106, can be configured to energize and de-energize electromagnets 801 with appropriate timing, so that a portion of flexible utility conduit 803 that leads from guide wheel 502 to connector 512 is held away from a portion of flexible utility conduit 503 that is disposed against conduit management surface 303.

Figure 9:
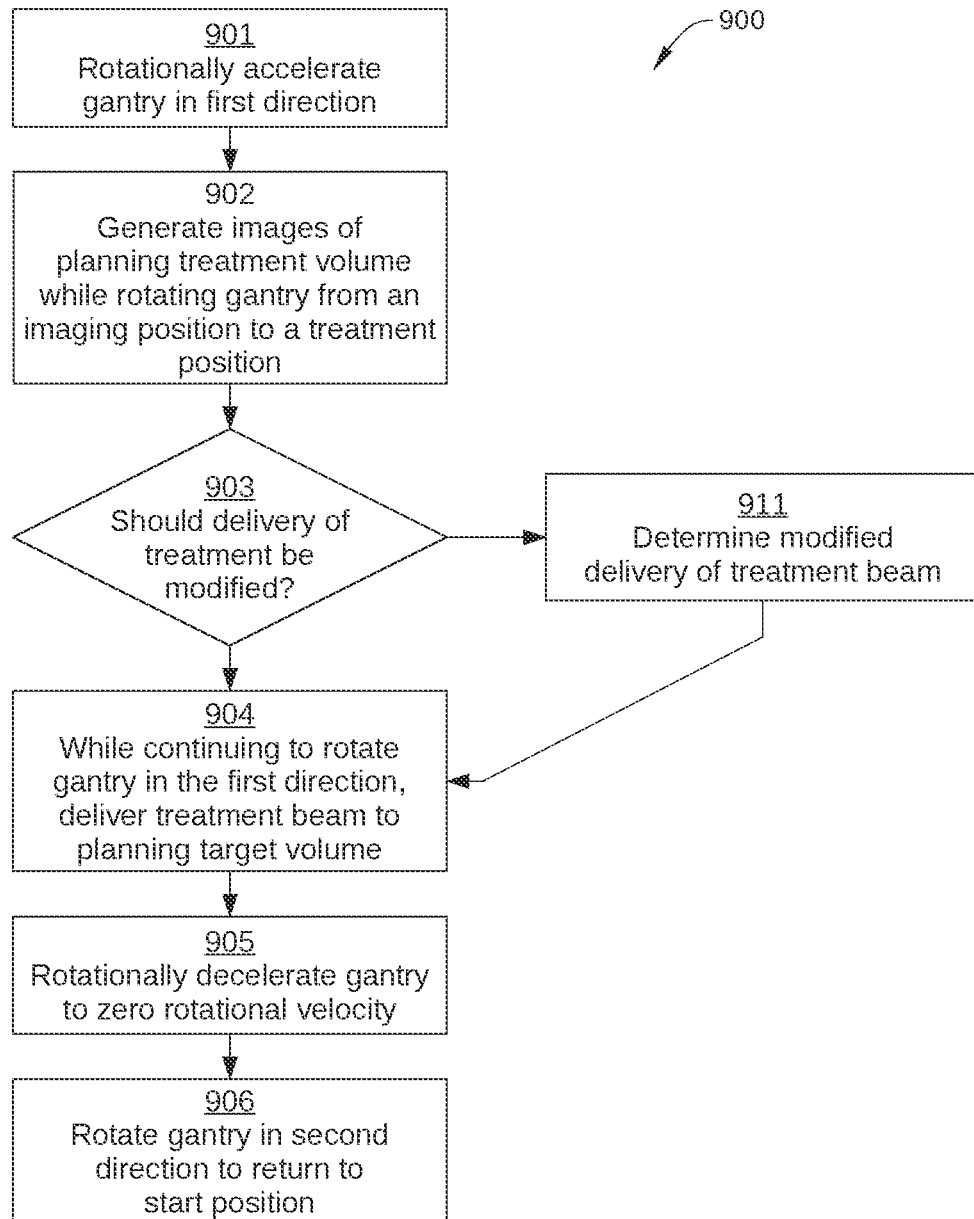
FIG. 9 sets forth a flowchart of an example method for radiation therapy in a radiation therapy system that includes a gantry with a treatment-delivering X-ray source and an imaging X-ray source mounted thereon, according to one or more embodiments of the present disclosure.

FIG. 9 sets forth a flowchart of an example method for radiation therapy in a radiation therapy system that includes a gantry with a treatment-delivering X-ray source and an imaging X-ray source mounted thereon, according to one or more embodiments of the present disclosure. The method may include one or more operations, functions, or actions as illustrated by one or more of blocks 901-911. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-8, persons skilled in the art will understand that any suitably configured radiation therapy system is within the scope of the present disclosure.

A method 900 begins at step 901, in which a computing device associated with RT system 100 (such as image acquisition and treatment control computer 106) causes gantry 300 to rotationally accelerate about bore 103 from no rotational velocity to a target rotational velocity while rotating in a specific direction (e.g., either clockwise or counterclockwise). In some embodiments, step 901 is synchronized with or initiated in response to the start of a patient breath-hold. In step 901, the gantry begins to rotationally accelerate from a start position, such as a radial position that is proximate one extent of the possible rotation of gantry 300. The acceleration may be constant or may be variable, such as an S-curve acceleration profile for reducing or eliminating jerk when reaching a target acceleration or deceleration. Generally, the rotational acceleration of gantry 300 ends when a target rotational velocity is achieved by gantry 300 and/or gantry 300 reaches a certain rotational location, such as an imaging position. In some embodiments, the target rotational velocity is reached after 5-20 degrees of rotation of gantry 300.

In step 902, while causing gantry 300 to continue rotating in the same direction as the rotational acceleration described in step 901, from the imaging position to a treatment position, the computing device causes multiple images of a target volume disposed in bore 103 to be generated using an imaging X-ray source of RT system 100. For example, in some embodiments, the target volume is a region surrounding and including a specific target tissue (a planning target volume), such as a cancerous tumor. In some embodiments, the generated images are projection images of the planning target volume. In some embodiments, the treatment position is separated from the first position in the current direction of rotation of gantry 300 by at least about one quarter rotation, or 90 degrees, of gantry 300.

In step 903, the computing device determines whether the current delivery of the treatment beam should be modified, based on the multiple images of the planning target volume generated in step 902. In some embodiments, a current position of the planning target volume can be determined based on the multiple images, for example, by performing digital tomosynthesis on the projection images generated in step 902. The current position can then be compared to a predicted position of the planning target volume, and position error of the planning target volume quantified. If the computing device determines that the current delivery of the treatment beam should be modified, method 900 proceeds to step 911; if not, method 900 proceeds to step 904. In some embodiments, modification of the treatment beam includes aborting the current treatment under certain conditions.

In step 904, the computing device causes gantry 300 to continue to rotate through the treatment position, and causes delivery of a treatment beam to the planning target volume to be initiated with a treatment-delivering X-ray source of RT system 100. In some embodiments, the computing device then causes the treatment to continue to be delivered until gantry 300 has completed a full revolution, i.e., a 360-degree arc from the treatment position to the treatment position. In embodiments in which the delivery of the treatment beam has been modified (see step 911), the computing device causes the modified treatment to be implemented in step 904. In yet another embodiment, a kV imaging process is interleaved with the delivery of the treatment beam, and as the treatment arc proceeds, images are continuously being updated, thereby checking that the planning target volume has not moved during the current breath-hold. In such embodiments, when the planning target volume has been determined to have moved beyond a threshold displacement, the computing device turns off the treatment beam. It is noted that, after gantry 300 has rotated past the treatment position, imaging can also take place and not just delivery of the treatment beam.

In step 905, after gantry 300 has completed the revolution from the treatment position to the treatment position, the computing device causes gantry 300 to rotationally decelerate from the target rotational velocity to no rotational velocity. The deceleration takes place while gantry 300 rotates in the current rotational direction from the treatment position to a stopping position. In some embodiments, the stopping position is radially proximate another extent of the possible rotation of gantry 300. In some embodiments, no rotational velocity is reached from the target rotational velocity after 5-20 degrees of rotation of gantry 300.

In step 906, after rotationally decelerating gantry 300 from the target rotational velocity to no rotational velocity, rotating gantry 300 in a second direction to the start position, where the second direction is opposite to the specific direction. That is, the computing device causes gantry 300 to rotate back to the start position described in step 901.

In step 911, which is performed in response to the computing device determining that the treatment beam should be modified, the computing device determines a modified delivery of the treatment beam, or aborts this attempt and the patient is asked to re-start a breath-hold with a different amount of air. In some embodiments, the modified delivery is based on the images generated in step 902.

Implementation of method 900 as described above enables radiation treatment and prepended image acquisition in a single pass of an extended-rotation gantry. Such radiation treatment can be more readily performed during a single breath-hold by a patient, thereby maximizing the number of patients who are able to undergo the radiation treatment.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A computer-implemented method of radiation therapy in a radiation therapy system that includes a gantry with a treatment-delivering X-ray source and an imaging X-ray source mounted thereon, the method comprising:
    rotating the gantry in a first direction at a first rotational velocity about an open bore of the radiation therapy system;
    while continuing to rotate the gantry in the first direction about the open bore from a first position to a treatment position, generating multiple images of a target volume disposed in the open bore using the imaging X-ray source; and
    upon rotating the gantry to the treatment position:
    initiating delivery of a treatment beam to the target volume with the treatment-delivering X-ray source; and
    continuing to rotate the gantry a complete revolution in the first direction from the treatment position to the treatment position while a first end of a flexible utility conduit is coupled to the treatment-delivering X-ray source and a second end of the flexible utility conduit is coupled to a connector mounted on a stationary drive stand rotatably coupled to the gantry.

2. The computer-implemented method of claim 1, further comprising, while rotating the gantry in the first direction at the first rotational velocity about the open bore, energizing an electromagnet that is coupled to a non-rotating surface of the stationary drive stand and is configured to separate a first portion of the flexible utility conduit from a second portion of the flexible utility conduit during rotation of the gantry.

3. The computer-implemented method of claim 1, wherein the radiation therapy system includes a conduit management cylinder that is configured to guide the flexible utility conduit from the treatment-delivering X-ray source to the connector mounted on the stationary drive stand.

4. The computer-implemented method of claim 3, wherein the radiation therapy system includes an annular support structure that rotates about the open bore and on which the conduit management cylinder is mounted, the method further comprising, while rotating the gantry in the first direction at the first rotational velocity, rotating the annular support structure about the open bore in the first direction at a second rotational velocity that is less than the first rotational velocity.

5. The computer-implemented method of claim 4, wherein the second rotational velocity is one half of the first rotational velocity.

6. The computer-implemented method of claim 1, further comprising, while continuing to rotate the gantry in the first direction from the treatment position, interleaving an imaging process with the delivery of the treatment beam.

7. A radiation treatment system comprising:
    a stationary drive stand;
    a gantry with a treatment-delivering X-ray source mounted thereon, wherein the gantry is rotatably coupled to the stationary drive stand and is configured to rotate in a first direction about a bore of the radiation treatment system at a first rotational velocity; and
    a processor configured to:
    cause the gantry to rotate in the first direction about the bore from a first position to a treatment position at the first rotational velocity while a first end of a flexible utility conduit is coupled to the treatment-delivering X-ray source and a second end of the flexible utility conduit is coupled to a connector mounted on the stationary drive stand; and
    causing the gantry to continue to rotate a complete revolution in the first direction about the bore from the treatment position to the treatment position while the first end of the flexible utility conduit is coupled to the treatment-delivering X-ray source and the second end of the flexible utility conduit is coupled to the connector mounted on the stationary drive stand.

8. The radiation treatment system of claim 7, wherein the processor is further configured to initiate delivery of a treatment beam to a target volume disposed in the bore using the treatment-delivering X-ray source.

9. The radiation treatment system of claim 7, further comprising a conduit management cylinder that is configured to guide the flexible utility conduit from the treatment-delivering X-ray source to the connector mounted on the stationary drive stand.

10. The radiation treatment system of claim 9, further comprising an annular support structure that rotates about the bore, wherein the conduit management cylinder is coupled to the annular support structure.

11. The radiation treatment system of claim 10, wherein the annular support structure is rotatably coupled to the stationary drive stand.

12. The radiation treatment system of claim 10, wherein the conduit management cylinder is rotatably coupled to the annular support structure.

13. The radiation treatment system of claim 10, wherein the conduit management cylinder is configured to guide the flexible utility conduit from the connector mounted on the stationary drive stand to the treatment-delivering X-ray source during rotation of the annular support structure.

14. The radiation treatment system of claim 10, further comprising at least one cable separator that is coupled to the annular support structure and is configured to separate a first portion of the flexible utility conduit from a second portion of the flexible utility conduit during rotation of the gantry.

15. The radiation treatment system of claim 14, wherein the at least one cable separator is rotatably coupled to the annular support structure.

16. The radiation treatment system of claim 14, wherein the at least one cable separator is positioned between a first portion of the flexible utility conduit that leads from a conduit management cylinder coupled to the annular support structure to the fixed connection on the stationary drive stand and a second portion of a flexible utility conduit that is disposed against a conduit management surface of the conduit management cylinder.

17. The radiation treatment system of claim 9, wherein the flexible utility conduit is routed for one-half turn around the conduit management cylinder.

18. The radiation treatment system of claim 7, further comprising at least one cable separator that is coupled to a non-rotating surface of the stationary drive stand and is configured to separate a first portion of the flexible utility conduit from a second portion of the flexible utility conduit during rotation of the gantry.

19. The radiation treatment system of claim 18, wherein the at least one cable separator includes an electromagnet that is configured to, when energized, attract a ferromagnetic plate that is coupled to the flexible utility conduit and separate a first portion of the flexible utility conduit from a second portion of the flexible utility conduit during rotation of the gantry.

20. The radiation treatment system of claim 19, wherein the electromagnet is positioned on the non-rotating surface of the stationary drive stand to align with the ferromagnetic plate coupled to the flexible utility conduit during rotation of the gantry.

* * * * *